United States Patent [19]
Klett-Loch

[11] Patent Number: 6,013,279
[45] Date of Patent: Jan. 11, 2000

[54] COMBINATION PREPARATION FOR STIMULATING THE GROWTH OF HAIR AND OPTIONALLY THE GROWTH OF SKIN AND NAILS AS WELL AS FOR PREVENTING OR ELIMINATING THE LOSS OF HAIR

[76] Inventor: Lore Maria Klett-Loch, Bautzener Weg 1-3, D-68309 Mannheim, Germany

[21] Appl. No.: 08/849,371

[22] PCT Filed: Dec. 7, 1995

[86] PCT No.: PCT/DE95/01745

§ 371 Date: Jun. 6, 1997

§ 102(e) Date: Jun. 6, 1997

[87] PCT Pub. No.: WO96/17584

PCT Pub. Date: Jun. 13, 1996

[30] Foreign Application Priority Data

Dec. 8, 1994 [DE] Germany ............................. 44 43 585
Mar. 15, 1995 [DE] Germany ............................ 195 09 354

[51] Int. Cl.⁷ ..................................................... A61K 9/48
[52] U.S. Cl. ......................... 424/451; 424/450; 424/401
[58] Field of Search .................................. 424/451, 450, 424/401

[56] References Cited

U.S. PATENT DOCUMENTS

| 4,863,950 | 9/1989 | Morganti | 514/419 |
| 5,597,575 | 1/1997 | Breitbarth | 424/401 |
| 5,741,518 | 4/1998 | Ribier et al. | 424/450 |

FOREIGN PATENT DOCUMENTS

| 2 704 394 | 11/1994 | France . |
| 23 31 456 | 1/1975 | Germany . |
| 34 17 136 | 2/1985 | Germany . |
| 2 052 450 | 7/1994 | Spain . |

OTHER PUBLICATIONS

Database WPI, Section Ch, Week 9429, Derwent Publications Ltd., Class D21, AN 94–236932.
Patent Abstracts of Japan, vol. 007, No. 014, Jan. 20, 1983, No. 57–171908 (Shizuya Shiozu), Oct. 22, 1982.
Patent Abstracts of Japan, vol. 008, No. 015, Jan. 21, 1984, No. 58–183614 (Shiseido KK), Oct. 26, 1983.
Patent Abstracts of Japan, vol. 008, No. 085, Apr. 18, 1984, No. 59–007111 (Shiseido KK), Jan. 14, 1984.
Patent Abstracts of Japan, vol. 001, No. 157, Dec. 14, 1977, No. JP52099223 (Eisai Co Ltd), Aug. 19, 1977.
Chemical Abstracts, vol. 114, No. 2, 1991, Abstract No. 11983w, "Hair preparations for preventing hair shedding in nonhuman mammals", p. 336.
Chemical Abstracts, vol. 100, No. 22, 1984, Abstract No. 179953w, "Hair preparations containing ubiquinones and peripheral vasodilators", p. 313.

*Primary Examiner*—Thurman K. Page
*Assistant Examiner*—Diedra Faulkner
*Attorney, Agent, or Firm*—Alston & Bird LLP

[57] ABSTRACT

A combination preparation for stimulating the growth of hair and, optionally, the growth of skin and nails with a combination of active ingredients comprising vitamins, enzymes, and amino acids develops its effects from within the body, in that the combination of active ingredients of the combination preparation is made as a component of a form of oral administration, and that it comprises at least: 1.25 wt. % provitamin A; 0.27 wt. % vitamin $B_1$; 5.25 wt. % vitamins of the $B_2$ group; 0.37 wt. % vitamin $B_6$; 0.001 wt. % vitamin $B_{12}$; 15.61 wt. % vitamin C; 2.5 wt. % vitamin E; 1.04 wt. % coenzyme Q 10; 0.02 wt. % methionine; and 0.018 wt. % cystine. To increase the effectiveness of the combination preparation, its use is described as a supplement to a topically applicable hair growth stimulant, in particular a thymus-containing therapeutical agent.

13 Claims, No Drawings

COMBINATION PREPARATION FOR STIMULATING THE GROWTH OF HAIR AND OPTIONALLY THE GROWTH OF SKIN AND NAILS AS WELL AS FOR PREVENTING OR ELIMINATING THE LOSS OF HAIR

The invention relates to a combination preparation for stimulating, on the one hand, the growth of hair and, optionally, the growth of skin and nails and for preventing or eliminating, on the other hand, the loss of hair to the extent that the hair follicles are still present or intact. More specifically, the combination preparation is a combination of active ingredients which contains vitamins, enzymes, and amino acids.

In practice, preparations for stimulating the growth of hair have been known for a long time, and they comprise a great variety of compositions. For example, such preparations may contain sulfur or sulfur compounds, vitamins, hormones, cholesterol- and lecithin-containing substances. On the one hand, such combination preparations are used for the preventive preservation and the health of the hair. On the other hand, however, they are also used for curing the loss of hair.

In both women and men, the occurrence of an increased loss of hair is accompanied by the fear of becoming totally bald-headed. Besides the medical aspect, disturbances in the hair growth thus present a great personal problem for the affected person. The rate of growth of the hair amounts to about 0.35 mm per day, the hair density is from about 80,000 to 150,000 hairs per head. A loss of 100 hairs per day constitutes already a pathological effluvium.

From hair follicles that remained intact, hair are able to regrow. However, during a multiphase, lengthy regrowth, hair follicles may shrink and lead to a gradual loss of hair.

For some years, Applicant has had on the market a GKL complex, whose combination of active ingredients is enriched with a high percentage of amino acids, enzymes, and vitamins B, E, and F. In particular, the known combination preparation contains an extract from calf thymus, vegetable extracts, and animal oils. The GKL complex of active ingredients has successfully been tested in numerous clinics and institutes by treating different forms of alopecia. One of the numerous publications appeared, for example, in the medical journal "Der Onkologe" (1/90), or in the special print of the medical journal "Der Deutsche Dermatologe" (11/93).

As a whole, is has resulted from several tests that the GKL complex of active ingredients is effective for all kinds of hair loss in men and women, that it prevents androgenic hair loss, avoids development of baldness and hair loss in cancer patients undergoing light to moderate chemotherapy and, moreover, that it also counteracts the development of dandruff.

The use of known hair growth stimulants in general and the GKL complex of active ingredients in particular is normally external. The forms of application of the known hair stimulants media are liquid. The flowable products are offered in the form of emulsions, lotions, shampoos, hair cures or hair tonics.

Also known are, when viewed alone, nutritional supplements, which serve to favorably influence the metabolism of the human body, and facilitate achieving purposeful effects. Nutritional supplements, which are directed to a dietetic use, are capable of effecting, for example, as a result of their composition, a protection against oxidation by bonding free radicals which develop to an increasing extent just in the case of a diet. The nutritional supplements become active within the body, in particular by resorption of endogenous cells.

Based on these interrelated topics, which are per se totally different, but form a complex of topics, it is the object of the present invention to describe a combination preparation of the kind under discussion, which spreads its effect from within the body into the body cells. To enhance the effectiveness of the combination preparation under discussion, at least with respect to stimulating the hair growth, a use of the combination preparation will also be described.

The combination preparation of the present invention is formulated such that its combination of active ingredients is a component of a form of administration for oral or even topical use, and that the combination of ingredients comprises approximately the following substances:

| | | |
|---|---|---|
| Provitamin A | 1.25 | wt. % |
| Vitamin $B_1$ | 0.27 | wt. % |
| Vitamins of the $B_2$ group | 5.25 | wt. % |
| Vitamin $B_6$ | 0.37 | wt. % |
| Vitamin $B_{12}$ | 0.001 | wt. % |
| Vitamin C | 15.61 | wt. % |
| Vitamin E | 2.5 | wt. % |
| Coenzyme Q 10 | 1.04 | wt. % |
| Methionine | 0.02 | wt. %, and |
| Cystine | 0.018 | wt %. |

The claimed combination preparation is used to supplement an already topically applicable hair growth stimulant, in particular a thymus-containing therapeutic agent.

The aforementioned thymus preparation with the GKL complex of active ingredients is applied exclusively externally. Proceeding from the basic effect of known nutritional supplements in the interior of the body, it has now been recognized that it is possible to influence in purposeful manner endogenous cells that are connected with the growth of hair, skin, and nails.

In accordance with the invention, a preparation for stimulating the growth of hair, skin, and nails, or a preparation for preventing or eliminating the loss of hair is capable of developing its effect within the body, when it contains on the one hand a composition that influences the body cells, and is present on the other hand in a form that can be introduced into the body. In this manner, it becomes possible to influence from within the activity of the hair follicles in the subcutis of the human being via resorption of active ingredients. In particular, it is possible to accelerate the multiphase, lengthy regrowth process, while largely avoiding a shrinkage of the hair follicles. Of essential importance is likewise the preventive effect of the combination preparation in accordance with the invention with respect to preserving the health of the hair, which proceeds along with a basic improvement of the hair structure.

Likewise, it has been recognized to be material to the invention that the effectiveness of the combination preparation can be considerably enhanced with respect to stimulating hair growth or preventing hair loss, when same is taken by mouth as a supplement to externally applicable hair growth stimulants. Likewise in this instance, a merely topical use is possible. In particular with respect to using the clinically tested GKL complex of active ingredients as described above in the background of the invention, it is possible to achieve a high effectiveness of the combination preparation. Finally, the use in accordance with the invention includes both an external and an internal treatment of the affected body cells. At this point, it should be emphasized that the thymus-containing therapeutic preparation may also be applied to the skin or the nails, so that even with respect to these indications, one can presume an enhanced effectiveness With respect to the composition of the combination of active ingredients is has also been recognized that the growth of cells in the areas of the body being treated can be positively influenced, when the furnished energy is optimally utilized. An optimal utilization of the furnished energy is promoted to a great extent by the interaction of different vitamins on the one hand and nutrients on the other hand. For example, the coenzyme Q 10 is particularly suited to improve the energy gain in the cell, since it is a so-called auxiliary substrate of the respiratory chain. Coenzyme Q 10 is in a position to both acquire and release electrons and to exchange same between the so-called cytochromes and flavoproteins. As an alternative, other substances are suitable as active ingredients, since they favor functions that are essential for the gain of energy in the cell.

In accordance with a particularly advantageous composition of the combination preparation, the combination of active ingredients includes different vitamins of the $B_2$ group. Considered in the combination of active ingredients are in particular nicotinamide, pantothenic acid, and riboflavin.

It has been found especially advantageous to consider for the combination of active ingredient vitamins of the $B_2$ group in the following amounts:

| | |
|---|---|
| Riboflavin | 0.35 wt. % |
| Nicotinamide | 3.75 wt. % |
| Folic acid | 0.09 wt. % |
| Pantothenic acid | 1.04 wt. % |
| Biotin | 0.02 wt. % |

It is possible to increase or decrease the dosage of individual ingredients.

Of very special advantage is the effect of the pantothenic acid which, by itself, is used for treating hair depigmentations and general dysfunctions of the skin, and which also promotes the healing of wounds. Especially preferred in the combination preparation of the present invention is the use of pantothenic acid from calcium pantothenate.

A further component of the combination of active ingredients includes the use of provitamin A, which is preferably beta carotene. As an alternative, mixed forms of the provitamin A from alpha-, beta-, or gamma-carotene could be also be present. At any rate, the provitamin A is changed in the organism which is able to produce the actual active ingredients. The provitamin A could again be obtained from vegetable raw materials. Possible suppliers of alpha- and beta-carotene are, for example, beets or carrots.

Vitamin $B_1$ which is proposed for the combination of active ingredients, is included in the formulation, preferably in the form of a salt, namely thiamine nitrate. Vitamin $B_6$, likewise contained in the combination of active ingredients, is present in the form of a salt, namely pyridoxine hydrochloride. Vitamin $B_6$, also named pyridoxine, is of very special importance insofar as inflammatory changes of the skin may occur, when there is an undersupply of vitamin $B_6$. Both in the case of vitamin $B_1$ and in the case of vitamin $B_6$, other salts or pure forms could also be of importance.

As regards a therapeutical application of vitamin $B_{12}$, same is used in the form of cyanocobalamin. In cyanocobalamin, the ligand is formed on the central cobalt atom of the compound by a CN group. In the place of vitamin $B_{12}$, it would also be possible to use vitamin $B_{12}$ analogs.

In accordance with a specially preferred embodiment, vitamin $B_{12}$ is involved in the form of a preparation with gelatin. The advantage of using a preparation from vitamin $B_{12}$ with gelatin over the use of vitamin $B_{12}$ as a pure substance lies in the handling and in the resistance of cyanocobalamin to light and air humidity. If the vitamin $B_{12}$-containing gelatin preparation is used in the combination of active ingredients, the percentage of vitamin $B_{12}$ in the gelatin corresponds to the actually required vitamin $B_{12}$ content in the combination of active ingredients. In the latter, the vitamin $B_{12}$-gelatin preparation amounts altogether to about 1.4 wt. %.

In the combination of active ingredients, vitamin C assumes a special place value. Preferably, use is made of vitamin C from calcium ascorbate. Calcium ascorbate is a calcium salt of the ascorbic acid and is commercially available. The special importance of vitamin C results in particular from the fact that ascorbic acid activates the growth of cells and, thus, likewise the growth of hair from the hair follicle.

As regards the highest effectiveness, an alpha-tocopherol compound is preferred in the case of the active ingredient vitamin E in the combination. D,L-alpha-tocopherol acetate is commercially available in synthetically produced form. The prefix "D,L indicates that the acetate compound is racemic at a certain position, i.e., optically active. It is preferred to use D,L-alpha-tocopherol acetate just because of its optically active configuration. Conceivable would be the possible use of alpha-tocopherol from natural, vegetable, or animal material.

The two amino acids contained in the combination of active ingredients, namely methionine and cystine, are used preferably in certain optically active configurations. They are on the one hand a racemic methionine and on the other hand an L-cystine. If methionine and cystine are used as pure substances in the combination of active ingredients, their amounts in the combination will be each 0.02 wt. %.

The two amino acids could also be components of a cereal or vegetable protein. However, it is preferred to add to the combination of active ingredients methionine and cystine as components of a milk protein.

It has been found very advantageous to use lactalbumin 80. Lactalbumin contains 80% proteins. The remainder of the preparation consists of milk sugar, fat, minerals, and water. The content of cystine or methionine in lactalbumin 80 is respectively 3.6% and 4%. When expressed in the weight unit mg, this means that 3.6% cystine correspond to 0.0864 mg and 4% methionine correspond to 0.096 mg. The percentage by weight of lactalbumin 80 being 0.62 in the combination of active ingredients, same contains 0.028 wt. % methionine and 0.018 wt. % cystine. The use of lactalbumin 80 permits almost total substitution of respectively 0.02% by weight of cystine and methionine as pure substances.

For the use of the combination preparation, it is possible to select from different forms of administration. Besides tablets or dragées, preferred are primarily capsules, which are filled with the combination of active ingredients. Advantageously, filling of the combination of active ingredients may be optimized in that the combination of active ingredients forms a preparation together with linseed oil. Except for converting the preparation to a pasty state, it is the function of the linseed oil to introduce essential fatty acids into the combination preparation and, finally into the human body, and to furnish the skin, the hair, and the nails with nutritional substances.

Furthermore, the combination preparation of the present invention may contain additional vegetable oils or fats as nutritional and carrier substances, which are both unmodified and hydrogenated. Likewise, these vegetable oils and fats are used on the one hand to ensure a fillability of the preparation and on the other hand to introduce essential fatty acids into the combination preparation. Besides unmodified linseed oil, the use of hydrogenated soybean oil and/or unmodified peanut oil has shown to be advantageous.

To be able to make the partially aqueous or powdery substances of the combination of active ingredient suspensible in the oily preparation, it is advantageous to add an emulsifier. The emulsifier may comprise, for example, a mixture of soybean lecithin and soybean phosphatides, which are already used in the food sector for a better solubility of powder in fluids.

The above-described preparation of the formulation, namely the conversion of the previously discussed ingredients of the combination preparation to a pasty state is directed to using capsules as a form of administration. Preferred in this instance are soft gelatin capsules.

Representative main ingredients required for preparing the capsule are gelatin and glycerol. Preferably, the unfilled capsule contains 85 wt. % glycerol. Furthermore, the capsule contains unmodified peanut oil as softener. Moreover, it is possible to involve a stabilizer, which has a preservative function. In particular, the stabilizer 420 has proved to be suitable for preparing the soft gelatin capsule.

Moreover, it is possible to add to the gelatin mass dyes (food dyes) and/or opacifiers (for example, titanium dioxide). of special advantage for use as dye is beta-carotene. In the this manner, the beta-carotene which is acts upon the body cell is also introduced as a capsule ingredient into the body.

In accordance with a preferred embodiment, a capsule has a weight of 480 mg. The weight distribution of the active ingredients in the combination and of the remaining substances over the total weight of 480 mg of the capsule, results therefrom, that the empty weight of the capsule falls slightly below the filling weight. This ensures an adequate stability of the capsule wall.

In accordance with the selected embodiment, a capsule having a total weight of 480 mg contains, on the average, 0.15 mg usable carbohydrates, 157.42 mg usable fats, and 98.46 mg usable proteins. The average physiological calorific value is about 1.9 kcal or 7.88 kJ per capsule.

Furthermore, it will be of advantage to supplement the combination of active ingredients with selenium or selenium yeast, whose weight can amount to as much as 5% of the entire combination of active ingredients. Selenium is a component of the enzyme glutathione peroxidase, which occurs in the erythrocytes (red blood cells) and protects so-called unsaturated cell membrane lipids against an attack of the oxygen molecule and other free radicals. Consequently, selenium is a part of the essential elements. An intake of selenium as selenium yeast is of advantage, since selenium can be better resorbed by accompanying substances of the yeast. Furthermore, yeast itself contains a relatively high percentage of the vitamin B complex.

The combination of active ingredients may comprise a thymus extract as an additional ingredient. The extract may be from cattle thymus as well as synthetically produced thymus peptides which are added preferably in spray-dried form. In the case of the thymus extract, the percentage by weight may amount to as much as 50% of the entire combination of active ingredients. In the case of thymus peptides, this percentage by weight may be reduced, so as not to exceed 5%. In this connection, it is very important that the addition of a thymus extract to the oral form of application assists the effect of an external application. This external application may be realized with the initially described product "Thymu-Skin."

When using synthetic thymus peptides, it is essential that same be isolated from the total extract. Accordingly, these peptides may be added to the preparation in synthetic form. While these peptides have qualitatively the same effect as the thymus extract itself, they preclude ineffective accompanying substances and may be used in small quantities.

Supplementing the foregoing, it should be pointed out that the combination preparation or the combination of active ingredients may contain "melatonin", which is associated with age-retarding properties, improvement of immune defenses, and with the effect as catalyst for influencing biological processes. Likewise, in this instance, it is presumed that the growth of hair, finger nails, and skin is promoted. This melatonin ingredient may be provided in a spectrum from 0.5 to about 30 mg.

Listed below are some of the above-described active ingredients with their nomenclature:

Vitamin B1 as thiamine nitrate; DAB, Ph.Eur., USP; vitamin B2 as riboflavin, DAB, Ph.Eur., USP; nicotinamide, DAB, Ph.Eur.; folic acid, DAB, Ph.Eur., USP; pantothenic acid from calcium pantothenate, DAB, Ph.Eur., USP; vitamin B6 as pyridoxine hydrochloride, DAB, Ph.Eur. USP; vitamin C from calcium ascorbate, FCC; racemic methionine, DAB, Ph.Eur., USP XI; and L-cystine, FCC.

Finally it should be remarked that the indicated amounts of the ingredients in the preparation combination may be quantitatively modified, be at least increased, and that the percentage distribution of individual ingredients may also be changed at least slightly.

I claim:

1. A composition for stimulating the growth of hair, stimulating the growth of skin and nails, and inhibiting the loss of hair, comprising, in a pharmaceutically acceptable carrier, approximately the following active ingredients:

| | | |
|---|---|---|
| Provitamin A | 1.25 | wt. % |
| Vitamin $B_1$ | 0.27 | wt. % |
| Vitamins of the $B_2$ group | 5.25 | wt. % |
| Vitamin $B_6$ | 0.37 | wt. % |
| Vitamin $B_{12}$ | 0.001 | wt. % |
| Vitamin C | 15.61 | wt. % |
| Vitamin E | 2.5 | wt. % |
| Coenzyme Q 10 | 1.04 | wt. % |
| Methionine | 0.02 | wt. %, and |
| Cystine | 0.018 | wt %. |

2. The composition as defined in claim 1 wherein the composition is in a form for oral administration.

3. The composition as defined in claim 1 wherein the composition is in a form for topical administration.

4. The composition as defined in claim 1 wherein the vitamins of the $B_2$ group comprise primarily nicotinamide, pantothenic acid, and riboflavin, and that the vitamins of the $B_2$ group comprise approximately the following ingredients

| | |
|---|---|
| Riboflavin | 0.35 wt. % |
| Nicotinamide | 3.75 wt. % |
| Folic acid | 0.09 wt. % |
| Pantothenic acid | 1.04 wt. % |
| Biotin | 0.02 wt. %, | the pantothenic acid being pantothenic acid from calcium pantothenate.

5. The composition as defined in claim 1 wherein the provitamin A is essentially beta-carotene, that the vitamin $B_1$ comprises thiamine nitrate, vitamin $B_6$ comprises pyridoxine hydrochloride, vitamin $B_{12}$ comprises cyanocobalamin and in a preparation with gelatin, the preparation of vitamin $B_{12}$ and gelatin amounting to about 1.04 wt. % of the combination of active ingredients.

6. The composition as defined in claim 1 wherein the vitamin C is vitamin C from calcium ascorbate, and that vitamin E is present in the form of D,L-alpha-tocopherol acetate, the methionine comprises racemic methionine and the cystine comprises L-cystine.

7. The composition as defined in claim 1 wherein methionine and cystine are contained in the combination of active ingredients as components of a milk protein, that the milk protein is lactalbumin 80, and that the lactalbumin 80 amounts to about 0.62 wt. % of the combination of active ingredients.

8. The composition as defined in claim 1 wherein the combination of active ingredients is present in a formulation with linseed oil for preparing the form of administration, and that the linseed oil is contained in the combination preparation in an amount of 25.0 wt. %.

9. The composition as defined in claim 1 wherein for preparing the form of administration, the combination of active ingredients is present in a formulation with modified and/or unmodified vegetable oils and/or in a formulation with an emulsifier.

10. The composition as defined in claim 1 wherein the composition is in the form of a capsule for oral administration, the capsule comprising at least gelatine and glycerol as well as a vegetable oil or fat and/or a stabilizer, that the capsule is dyed, and the filled capsule has a total weight of about 480 mg, the composition comprising approximately the following additional active ingredients:

| | |
|---|---|
| Beta-carotene | 6.0 mg |
| Vitamin B1 as thiamine nitrate | 1.3 mg |
| Vitamin B2 as riboflavin | 1.7 mg |
| Nicotinamide | 18.0 mg |
| Folic acid | 0.45 mg |
| Pantothenic acid from calcium pantothenate | 5.0 mg |
| Biotin | 0.1 mg |
| Vitamin B6 as pyridoxine hydrochloride | 1.8 mg |
| Vitamin B12 as cyanocobalamin 0.1% with gelatin | 5.0 mg |
| Vitamin C from calcium ascorbate | 75.0 mg |
| Vitamin E as D,L-alpha-tocopherol acetate | 12.0 mg |
| Coenzyme Q 10 | 5.0 mg |
| Lactalbumin 80 with 3.6% cystine and 4% methionine in 80% protein of the lactalbumin and the adjuvants: | 3.0 mg, |
| Linseed oil | 120.0 mg as well as |
| Emulsifier E 322 | |
| Gelatin | |
| Vegetable oils (partially hydrogenated) | 225.65 mg |
| Glycerol (85%) | |
| Stabilizer E 420 | |
| Beta-carotene as dye. | |

11. The composition as defined in claim 1 wherein the combination of active ingredients comprises the component selenium or selenium yeast, that the selenium or selenium yeast is contained in an amount of up to 5% by weight of the total combination of active ingredients, that the combination of active ingredients comprises a thymus extract, and that the thymus extract is an extract from cattle thymus or synthetically produced thymus peptides, the thymus extract amounting up to about 50% by weight of the total combination of active ingredients, or the thymus peptides amounting up to about 5% by weight of the total combination of active ingredients.

12. The composition as defined in claim 1 wherein the combination of active ingredients comprises the component melatonin, and the active ingredient melatonin is provided in a range from 0.5 to 30 mg.

13. A method of using the composition as defined in claim 1, comprising the step of using the composition as a supplement to a topically applicable stimulant comprising a thymus-containing therapeutical agent for the growth of hair and, optionally, the growth of skin and nails.

* * * * *